(12) United States Patent
Liu et al.

(10) Patent No.: US 11,505,607 B2
(45) Date of Patent: Nov. 22, 2022

(54) BISPECIFIC SINGLE-CHAIN ANTIBODY, RECOMBINANT ONCOLYTIC VIRUS FOR EXPRESSING SAME AND VIRUS COMPOSITION

(71) Applicant: BINHUI BIOPHARMACEUTICAL CO., LTD., Wuhan (CN)

(72) Inventors: Binlei Liu, Wuhan (CN); Linkang Cai, Wuhan (CN); Runyang Wang, Wuhan (CN); Siqi Zhang, Wuhan (CN); Han Hu, Wuhan (CN)

(73) Assignee: BINHUI BIOPHARMACEUTICAL CO., LTD., Wuhan (CN)

( * ) Notice: Subject to any disclaimer, the term of this patent is extended or adjusted under 35 U.S.C. 154(b) by 0 days.

(21) Appl. No.: 17/568,738

(22) Filed: Jan. 5, 2022

(65) Prior Publication Data

US 2022/0153843 A1     May 19, 2022

Related U.S. Application Data

(63) Continuation of application No. PCT/CN2021/130773, filed on Nov. 15, 2021.

(30) Foreign Application Priority Data

Nov. 13, 2020 (CN) .......................... 202011265931.6

(51) Int. Cl.
*C12N 7/00*      (2006.01)
*C07K 16/28*     (2006.01)

(52) U.S. Cl.
CPC ...... *C07K 16/2809* (2013.01); *C07K 16/2827* (2013.01); *C12N 7/00* (2013.01); *C07K 2317/31* (2013.01); *C07K 2317/622* (2013.01); *C12N 2710/16621* (2013.01); *C12N 2710/16632* (2013.01); *C12N 2710/16643* (2013.01)

(58) Field of Classification Search
CPC .................................................. C07K 16/2809
USPC .................................................... 424/136.1
See application file for complete search history.

(56) References Cited

U.S. PATENT DOCUMENTS

2019/0169296 A1*   6/2019   Russell .............. C07K 16/2809

FOREIGN PATENT DOCUMENTS

| CN | 104829729 A | * | 8/2015 |
| CN | 112430271 B | | 9/2021 |
| WO | WO 2019/023483 A1 | * | 1/2019 |

* cited by examiner

*Primary Examiner* — Sean E Aeder

(57) ABSTRACT

The present disclosure provides a bispecific single-chain antibody, recombinant oncolytic virus for expressing same and virus composition. The antibody named BiTEs-PD-L1 is a bispecific antibody capable of simultaneously binding CD3 and PD-L1 on the surfaces of tumor cells, and it can effectively activate T cells and guide T cells to kill tumor cells. The oncolytic virus oHSV2-BiTEs-PD-L1 is further developed by utilizing the BiTEs-PD-L1, it can reduce frequency and dosage of the administration. The present disclosure also confirmed several virus compositions with excellent antitumor effect.

3 Claims, 11 Drawing Sheets

Specification includes a Sequence Listing.

SEQUENCE LISTING

<160> NUMBER OF SEQ ID NOS: 5

<210> SEQ ID NO 1
<211> LENGTH: 515
<212> TYPE: PRT
<213> ORGANISM: Artificial Sequence
<220> FEATURE:
<223> OTHER INFORMATION: Synthetic Polyaminoacid -continued

```
<400> SEQUENCE: 1

Met Asn Phe Gly Leu Ser Leu Ile Phe Leu Val Leu Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Ser Trp Ile His Trp Val Arg Gln Ala Pro Gly Lys Gly Leu
    50                  55                  60

Glu Trp Val Ala Trp Ile Ser Pro Tyr Gly Gly Ser Thr Tyr Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ala Arg Arg His Trp Pro Gly Gly Phe Asp Tyr Trp Gly
        115                 120                 125

Gln Gly Thr Leu Val Thr Val Ser Ala Ala Gly Gly Gly Gly Ser Gly
    130                 135                 140

Gly Gly Gly Ser Gly Gly Gly Gly Ser Asp Ile Gln Met Thr Gln Ser
145                 150                 155                 160

Pro Ser Ser Leu Ser Ala Ser Val Gly Asp Arg Val Thr Ile Thr Cys
                165                 170                 175

Arg Ala Ser Gln Asp Val Ser Thr Ala Val Ala Trp Tyr Gln Gln Lys
            180                 185                 190

Pro Gly Lys Ala Pro Lys Leu Leu Ile Tyr Ser Ala Ser Phe Leu Tyr
        195                 200                 205

Ser Gly Val Pro Ser Arg Phe Ser Gly Ser Gly Ser Gly Thr Asp Phe
210                 215                 220

Thr Leu Thr Ile Ser Ser Leu Gln Pro Glu Asp Phe Ala Thr Tyr Tyr
225                 230                 235                 240

Cys Gln Gln Tyr Leu Tyr His Pro Ala Thr Phe Gly Gln Gly Thr Lys
                245                 250                 255

Val Glu Ile Lys Arg Thr Gly Gly Gly Ser Asp Ile Lys Leu Gln Gln
            260                 265                 270

Ser Gly Ala Glu Leu Ala Arg Pro Gly Ala Ser Val Lys Met Ser Cys
        275                 280                 285

Lys Thr Ser Gly Tyr Thr Phe Thr Arg Tyr Thr Met His Trp Val Lys
    290                 295                 300

Gln Arg Pro Gly Gln Gly Leu Glu Trp Ile Gly Tyr Ile Asn Pro Ser
305                 310                 315                 320

Arg Gly Tyr Thr Asn Tyr Asn Gln Lys Phe Lys Asp Lys Ala Thr Leu
                325                 330                 335

Thr Thr Asp Lys Ser Ser Ser Thr Ala Tyr Met Gln Leu Ser Ser Leu
            340                 345                 350

Thr Ser Glu Asp Ser Ala Val Tyr Tyr Cys Ala Arg Tyr Tyr Asp Asp
        355                 360                 365

His Tyr Cys Leu Asp Tyr Trp Gly Gln Gly Thr Thr Leu Thr Val Ser
    370                 375                 380

Ser Val Glu Gly Gly Ser Gly Gly Ser Gly Gly Ser Gly Gly Ser Gly
385                 390                 395                 400

Gly Val Asp Asp Ile Gln Leu Thr Gln Ser Pro Ala Ile Met Ser Ala
                405                 410                 415
```

```
Ser Pro Gly Glu Lys Val Thr Met Thr Cys Arg Ala Ser Ser Val
            420                 425                 430

Ser Tyr Met Asn Trp Tyr Gln Gln Lys Ser Gly Thr Ser Pro Lys Arg
            435                 440                 445

Trp Ile Tyr Asp Thr Ser Lys Val Ala Ser Gly Val Pro Tyr Arg Phe
        450                 455                 460

Ser Gly Ser Gly Ser Gly Thr Ser Tyr Ser Leu Thr Ile Ser Ser Met
465                 470                 475                 480

Glu Ala Glu Asp Ala Ala Thr Tyr Tyr Cys Gln Gln Trp Ser Ser Asn
                485                 490                 495

Pro Leu Thr Phe Gly Ala Gly Thr Lys Leu Glu Leu Lys His His His
            500                 505                 510

His His His
       515

<210> SEQ ID NO 2
<211> LENGTH: 1764
<212> TYPE: DNA
<213> ORGANISM: Artificial Sequence
<220> FEATURE:
<223> OTHER INFORMATION: Synthetic Polynucleotide

<400> SEQUENCE: 2
atgtgtcctc agaagctaac catctcctgg tttgccatcg ttttgctggt gtcccactc      60 atggccatgt gggagctgga aaagacgtt tatgttgtag aggtggactg gactcccgat     120 gccctggag aaacagtgaa cctcacctgt gacacgcctg aagaagatga catcacctgg     180
acctcagacc agagacatgg agtcataggc tctggaaaga ccctgaccat cactgtcaaa     240
gagtttctag atgctggcca gtacacctgc acaaaggag gcgagactct gagccactca     300
catctgctgc tccacaagaa ggaaaatgga atttggtcca ctgaaatttt aaaaaatttc     360
aaaaacaaga ctttcctgaa gtgtgaagca ccaaattact ccggacggtt cacgtgctca     420
tggctggtgc aaagaaacat ggacttgaag ttcaacatca gagcagtag cagttcccct     480 gactctcggg cagtgacatg tggaatgcg tctctgtctg cagagaaggt cacactggac     540
caaagggact atgagaagta ttcagtgtcc tgccaggagg atgtcacctg cccaactgcc     600
gaggagaccc tgcccattga actggcgttg aagcacggc agcagaataa atatgagaac     660
tacagcacca gcttcttcat cagggacatc atcaaaccag acccgcccaa gaacttgcag     720
atgaagcctt tgaagaactc acaggtggag gtcagctggg agtaccctga ctcctggagc     780
actccccatt cctacttctc cctcaagttc tttgttcgaa tccagcgcaa gaaagaaaag     840
atgaaggaga cagaggaggg gtgtaaccag aaaggtgcgt tcctcgtaga aagacatct     900 accgaagtcc aatgcaaagg cgggaatgtc tgcgtgcaag ctcaggatcg ctattacaat     960
tcctcgtgca gcaagtgggc atgtgttccc tgcagggtcc gatccggcgg tggcggtgga    1020
agcggcggtg gcggaagcgg cggtggcggc agcatggtca cgttccaac agcctcaccc   1080 tcggcatcca gcagctcctc tcagtgccgg tccagcatgt gtcaatcacg ctacctcctc   1140
tttttggcca cccttgccct cctaaaccac ctcagtttgg ccagggtcat tccagtctct   1200
ggacctgcca ggtgtcttag ccagtcccga aacctgctga agaccacaga tgacatggtg   1260
aagacggcca gagaaaaact gaaacattat tcctgcactg ctgaagacat cgatcatgaa   1320
gacatcacac gggaccaaac cagcacattg aagacctgtt taccactgga actacacaag   1380
aacgagagtt gcctggctac tagagagact tcttccacaa caagagggag ctgcctgccc   1440
```

```
ccacagaaga cgtctttgat gatgaccctg tgccttggta gcatctatga ggacttgaag   1500
atgtaccaga cagagttcca ggccatcaac gcagcacttc agaatcacaa ccatcagcag   1560
atcattctag acaagggcat gctggtggcc atcgatgagc tgatgcagtc tctgaatcat   1620
aatggcgaga ctctgcgcca gaaacctcct gtgggagaag cagacccta cagagtgaaa    1680 atgaagctct gcatcctgct tcacgccttc agcacccgcg tcgtgaccat caacagggtg   1740
atgggctatc tgagctccgc ctga                                         1764
```

<210> SEQ ID NO 3
<211> LENGTH: 426
<212> TYPE: DNA
<213> ORGANISM: Artificial Sequence
<220> FEATURE:
<223> OTHER INFORMATION: Synthetic Polynucleotide

<400> SEQUENCE: 3

```
atgtaccgga tgcagctgct gagctgcatc gccctgagcc tggccctggt gaccaacagc     60
atgggcagca gccaccacca ccaccaccac agcagcggcc tggtgccccg ggcagccac    120 atgcccaaga agaagatcca gctgcacgcc gagcacgccc tgtacgacgc cctgatgatc   180
ctgaacatcg tgaagaccaa cagccccccc gccgaggaga gctggagga ctacgccttc    240 aacttcgagc tgatcctgga ggagatcgcc cggctgttcg agagcggcga ccagaaggac   300
gaggccgaga aggccaagcg gatgaaggag tgatgaagg ggatcaagac caccgccagc    360
gaggacgagc aggaggagat ggccaacgcc atcatcacca tcctgcagag ctggatcttc   420
agctga                                                             426
```

<210> SEQ ID NO 4
<211> LENGTH: 906
<212> TYPE: DNA
<213> ORGANISM: Artificial Sequence
<220> FEATURE:
<223> OTHER INFORMATION: Synthetic Polynucleotide

<400> SEQUENCE: 4

```
atgcagatcc cccaggcccc ctggcccgtg gtgtgggccg tgctgcagct gggctggcgg     60
cccggctggt tcctggacag cccccgaccgg ccctggaacc cccccacctt cagccccgcc   120
ctgctggtgg tgaccgaggg cgacaacgcc accttcacct gcagcttcag caacaccagc   180
gagagcttcc acgtggtgtg caccgggag agccccagcg ccagaccga caccctggcc     240 gccttccccg aggaccggag ccagcccggc caggactgcc ggttccgggt gacccagctg   300
cccaacggcc gggacttcca catgagcgtg gtgcgggccc ggcggaacga cagcggcacc   360
tacgtgtgcg gcgtgatcag cctggccccc aagatccaga tcaaggagag cctgcgggcc   420
gagctgcggg tgaccgagcg gcgggccgag gtgcccaccg cccacccag cccagcccc    480 cggcccgccg ccagttcca gaccctggag cccaagagct cgacaagac ccacacctgc    540 cccccctgcc ccgcccccga gctgctgggc ggccccagcg tgggccagcc ccgggagccc   600
caggtgtaca ccctgccccc cagccgggac gagctgacca gaaccaggt gagcctgacc   660 tgcctggtga gggcttcta ccccagcgac atcgccgtgg agtgggagag caacggccag   720
cccgagaaca actacaagac cacccccccc gtgctggaca gcgacggcag cttcttcctg   780
tacagcaagc tgaccgtgga caagagccgg tggcagcagg gcaacgtgtt cagctgcagc   840
gtgatgcacg aggccctgca caaccactac acccagaaga gcctgagcct gagccccggc   900
```

| aagtaa | 906 |

<210> SEQ ID NO 5
<211> LENGTH: 2067
<212> TYPE: DNA
<213> ORGANISM: Artificial Sequence
<220> FEATURE:
<223> OTHER INFORMATION: Synthetic Polynucleotide

<400> SEQUENCE: 5

| atgcaggtgc agctggtgca gagcggcgtg gaggtgaaga agcccggcgc cagcgtgaag | 60 |
| gtgagctgca aggccagcgg ctacaccttc accaactact acatgtactg ggtgcggcag | 120 |
| gccccggcc agggcctgga gtggatgggc ggcatcaacc ccagcaacgg cggcaccaac | 180 |
| ttcaacgaga agttcaagaa ccgggtgacc ctgaccaccg acagcagcac caccaccgcc | 240 |
| tacatggagc tgaagagcct gcagttcgac gacaccgccg tgtactactg cgcccggcgg | 300 |
| gactaccggt tcgacatggg cttcgactac tggggccagg gcaccaccgt gaccgtgagc | 360 |
| agcgccagca ccaagggccc cagcgtgttc cccctggccc cctgcagccg gagcaccagc | 420 |
| gagagcaccg ccgccctggg ctgcctggtg aaggactact cccccgagcc cgtgaccgtg | 480 |
| agctggaaca gcggcgccct gaccagcggc gtgcacacct tccccgccgt gctgcagagc | 540 |
| agcggcctgt acagcctgag cagcgtggtg accgtgccca gcagcagcct gggcaccaag | 600 |
| acctacacct gcaacgtgga ccacaagccc agcaacacca aggtggacaa gcgggtggag | 660 |
| agcaagtacg gcccccctg ccccccctgc cccgcccccg agttcctggg cggccccagc | 720 |
| gtgttcctgt tccccccaa gcccaaggac accctgatga tcagccggac ccccgaggtg | 780 |
| acctgcgtgg tggtggacgt gagccaggag gaccccgagg tgcagttcaa ctggtacgtg | 840 |
| gacggcgtgg aggtgcacaa cgccaagacc aagcccgg aggagcagtt caacagcacc | 900 |
| taccgggtgg tgagcgtgct gaccgtgctg caccaggact ggctgaacgg caaggagtac | 960 |
| aagtgcaagg tgagcaacaa gggcctgccc agcagcatcg agaagaccat cagcaaggcc | 1020 |
| aagggccagc ccgggagcc ccaggtgtac accctgcccc cagccagga ggagatgacc | 1080 |
| aagaaccagg tgagcctgac ctgcctggtg aagggcttct accccagcga catcgccgtg | 1140 |
| gagtgggaga gcaacggcca gcccgagaac aactacaaga ccacccccc cgtgctggac | 1200 |
| agcgacggca gcttcttcct gtacagccgg ctgaccgtgg acaagagccg gtggcaggag | 1260 |
| ggcaacgtgt tcagctgcag cgtgatgcac gaggccctgc acaaccacta cacccagaag | 1320 |
| agcctgagcc tgagcctggg caagggcagc ggcgccacca acttcagcct gctgaagcag | 1380 |
| gccggcgacg tggaggagaa ccccggcccc gagatcgtgc tgacccagag ccccgccacc | 1440 |
| ctgagcctga gcccggcga gcgggccacc ctgagctgcc gggccagcaa gggcgtgagc | 1500 |
| accagcggct acagctacct gcactggtac cagcagaagc ccggccaggc ccccggctg | 1560 |
| ctgatctacc tggccagcta cctggagagc ggcgtgcccg ccggttcag cggcagcggc | 1620 |
| agcggcaccg acttcacct gaccatcagc agcctggagc ccgaggactt cgccgtgtac | 1680 |
| tactgccagc acagccggga cctgcccctg accttcggcg gcggcaccaa ggtggagatc | 1740 |
| aagcggaccg tggccgcccc cagcgtgttc atcttccccc cagcgacga gcagctgaag | 1800 |
| agcggcaccg ccagcgtggt gtgcctgctg aacaacttct accccgggga ggccaaggtg | 1860 |
| cagtggaagg tggacaacgc cctgcagagc ggcaacagcc aggagagcgt gaccgagcag | 1920 |
| gacagcaagg acagcaccta cagcctgagc agcaccctga ccctgagcaa ggccgactac | 1980 |

-continued

```
gagaagcaca aggtgtacgc ctgcgaggtg acccaccagg gcctgagcag ccccgtgacc    2040
aagagcttca accggggcga gtgctaa                                        2067
```

BISPECIFIC SINGLE-CHAIN ANTIBODY, RECOMBINANT ONCOLYTIC VIRUS FOR EXPRESSING SAME AND VIRUS COMPOSITION

The present application is a continuation-application of International Patent Application (PCT) No. PCT/CN2021/130773 filed on Nov. 15, 2021, which claims foreign priority of Chinese Patent Application No. 202011265931.6, filed on Nov. 13, 2020, the entire contents of which are hereby incorporated by reference.

SEQUENCE LISTING

The instant application contains a Sequence Listing which has been submitted electronically in ASCII format and is hereby incorporated by reference in its entirety. Said ASCII copy, created on Nov. 15, 2021, is named SY1US214256 SL.txt and is 12,295 bytes in size.

TECHNICAL FIELD

The present disclosure relates to the field of biotechnology, in particular to a bispecific single-chain antibody, recombinant oncolytic virus for expressing same and virus composition.

BACKGROUND

BiTEs (bispecific T cell engagers) is a bispecific single-chain antibody taking T cells as effector cells, has two antigen binding arms, can be simultaneously bound with the T cells and target cells, and can activate cytotoxic T cells to kill diseased cells. Compared with other bispecific antibodies, the BiTEs has better molecular flexibility, can better promote the connection of a CD3 complex and a tumor target, is not restricted by a T cell receptor and MHC class I molecules on target cells, does not need the participation of costimulatory molecules, and is an antibody form with great application potential.

Herpes simplex virus (HSV) is a double stranded DNA virus with a length of about 154 kb, which can replicate in the infected host nucleus. RSV vector has the following advantages: 1) vide host cells; 2) high virus titer; 3) large foreign gene capacity. The disadvantage of HSV vector is its toxicity.

The prior art provides a variety of recombinant oncolytic viruses loaded with different functional genes with HSV type II as the vector.

SUMMARY

The present disclosure aims to provide a bispecific single-chain antibody, recombinant oncolytic virus for expressing same and virus composition.

In order to achieve the purpose, one aspect of the disclosure is directed to a bispecific single-chain antibody. The bispecific single-chain antibody, comprising a CD3 binding site and a PD-L1 binding site, and is called BiTEs-PD-L1 for short.

In some embodiments of the present disclosure, the amino acid sequence of the bispecific single-chain antibody is as shown in SEQ ID No. 1.

The second aspect of the present disclosure is directed to an application of the bispecific single-chain antibody in preparation of antitumor drugs. The BiTEs-PD-L1 provided by the present disclosure is a bispecific antibody capable of simultaneously binding CD3 and PD-L1 on the surfaces of tumor cells, and when the BiTEs-PD-L1 enters a body and is bound with the T cells, the T cells can be effectively activated, and the T cells are guided to kill the tumor cells. When BiTEs-PD-L1 is bound with the tumor cells, the tumor cells can be exposed, the T cells are attracted to kill the tumor cells, meanwhile, immunosuppression of PD-1/PD-L1 can be relieved, and depletion of the T cells is delayed.

The third aspect of the present disclosure is directed to a recombinant oncolytic virus carrying a gene of the bispecific single-chain antibody, the recombinant oncolytic virus includes a herpes simplex virus type II as a vector, and a coding gene of the bispecific single-chain antibody is integrated in the vector, it is named oHSV2-BiTEs-PD-L1.

In some embodiments of the present disclosure, the recombinant oncolytic virus is a herpes simplex virus type II HG52dICP47d34.5-BiTEs-PDL-1, and its accession number is CCTCC (China Center for Type Culture Collection) NO: V202053. It is preserved in China Center for Type Culture Collection in Wuhan University on Sep. 8, 2020.

The vector is a recombinant herpes simplex virus type II with ICP 34.5 region and ICP 47 region knocked out, and a BiTEs-PD-L1 gene is integrated into the knocked-out ICP 34.5 region by utilizing a plasmid pHG52d34.5-CMV-BiTEs-PD-L1 in a homologous recombination manner (On the premise of knowing the bites-pd-11 sequence, those skilled in the art can easily construct the vector plasmid). Because the bispecific single-chain antibody gene is integrated into the oncolytic virus, the bispecific single-chain antibody can be expressed in vivo for a long time, and the longest expression can reach 7 days.

The fourth aspect of the present disclosure is directed to a virus composition, comprising two or more recombinant herpes simplex viruses loaded with different functional genes, one of the virus is oHSV2-BiTEs-PD-L1.

In some embodiments of the present disclosure, the virus composition also includes one or more selected from the group consisting of oHSV2-hGM-CSF, oHSV2-OX40L, oHSV2-PD1v, oHSV2-neo and oHSV2-IL12. Preferably, the virus composition is oHSV2-BiTEs-PD-L1 and oHSV2-hGM-CSF. Specifically, oHSV2-hGM-CSF is preserved, and its accession number is CGMCC no. 3600; More preferably, the virus composition is oHSV2-BiTEs-PD-L1, oHSV2-hGM-CSF and oHSV2-OX40L. oHSV2-OX40L is based on oHSV2-hGM-CSF, and insert foreign gene (GenBank: BC153120 1) into it.

The fifth aspect of the present disclosure is directed to a virus composition, comprising oHSV2-hGM-CSF and oHSV2-OX40L. In some embodiments of the present disclosure, the virus composition also includes one or more selected from the group consisting of oHSV2-PD1v, oHSV2-neo and oHSV2-IL12.

The sixth aspect of the present disclosure is directed to a virus composition, comprising oHSV2-PD1v, oHSV2-neo and oHSV2-IL12.

In some embodiments of the present disclosure, oHSV2-PD1v is based on oHSV2-hGM-CSF, and insert foreign gene (SEQ ID No. 4) into it; oHSV2-neo is based on oHSV2-hGM-CSF, and insert foreign gene (SEQ ID No. 3) into it. oHSV2-IL12 is based on oHSV2-hGM-CSF, and insert foreign gene (SEQ ID No. 2) into it.

The beneficial effects of the present disclosure are as follows:

1. BiTEs-PD-L1 can effectively activate T cells and guide T cells to kill tumor cells.

2. oHSV2-BiTEs-PD-L1 can specifically proliferate in the tumor cells, the oncolytic virus has the characteristics of high safety and simple preparation process, the half-life period of the BiTEs-PD-L1 in an organism is prolonged, and the administration frequency and the administration dosage are reduced.

3. The efficacy of a variety of virus compositions loaded with different functional genes was detected, and several virus compositions with excellent antitumor effect were confirmed.

DETAILED DESCRIPTION OF THE EMBODIMENTS

The present disclosure is further described in detail in combination with drawings and specific embodiments. The following embodiments are implemented on the premise of the technical solution, a detailed implementation mode and a specific operation process are provided, but the protection range of the present disclosure is not limited to the following embodiments.

Part I BiTEs-PD-L1 and oHSV2-BiTEs-PD-L1

Embodiment 1

A Process of BiTEs-PD-L1 Preparation

A pHG52d34.5-CMV-BiTEs-PD-L1 plasmid is transfected into HEK-293T by using a calcium phosphate transfection reagent, supernatants are collected after 48 hours and 72 hours, and BiTEs-PD-L1 in the supernatants is adsorbed by using a Ni-NTA affinity chromatography medium (AKTA); a washing buffer solution (50 mM of $Na_2HPO_4$, 0.3 M of NaCl and 10 mM of imidazole with a pH value of 8.0) and an elution buffer solution (50 mM of $Na_2HPO_4$, 0.3 M of NaCl and 250 mM of imidazole with a pH value of 8.0) are used for eluting the BiTEs-PD-L1 from the medium; and the obtained product is dialyzed by using a 20 kDa dialysis card, the dialyzed product is replaced in a PBS buffer solution, and the dialyzed product is cryopreserved at −70° C.

Embodiment 2

Figure 1:
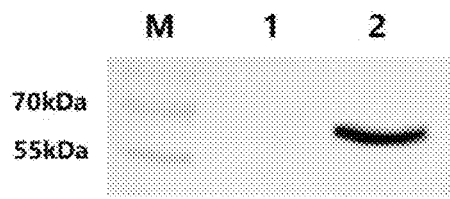
FIG. 1 is an electrophoresis purification diagram of BiTEs-PD-L1.

BiTEs-PD-L1 Western Identification 1) a collected protein sample is uniformly mixed with a 4×SDS-PAGE protein loading buffer solution, and the obtained mixture is boiled for 10 minutes;

(2) SDS-PAGE gel and 12% separation gel are prepared, 5 μL of a protein Marker and 6 μL of a sample are respectively added into a sample application hole, electrophoresis is started, the voltage of the upper layer gel is controlled to be 80V and the voltage of the lower layer gel is controlled to be 120V, and electrophoresis is stopped when bromophenol blue reaches the bottom; the result is as shown in FIG. 1, a first lane is a negative control sample, and a second lane is a BiTEs-PD-L1 sample (55 kDa);

3) after the electrophoresis is finished, gel cutting is carried out to remove upper-layer gel and redundant gel, and meanwhile, the bromophenol blue part at the bottom end is cut off;

4) filter paper and an NC (nitrocellulose) membrane are cut, the size of the NC membrane is enabled to be equal to that of the gel, small filter paper is enabled to be slightly smaller than that of the gel, and the NC membrane, albumen glue and the filter paper are immersed into a membrane transfer buffer solution; the large filter paper, the NC membrane, the albumen glue and the small filter paper (the filter paper cannot be in contact with one another and does not have bubbles) are sequentially placed on a membrane transfer instrument, and membrane transfer is conducted for 15 min under 15 V;

5) after the membrane transfer is completed, washing is conducted for three times by using PBST (PBS+0.05% Tween 20), wherein washing is conducted for 10 minutes each time;

6) sealing: sealing is conducted for 2 hours at 37° C. by using sealing liquid (5 g of skim milk powder+100 mL of PBST); after sealing is finished, the sample is placed on a shaking table and washed with PBST for three times, wherein washing is conducted for 10 minutes each time;

7) a mouse 6×His antibody is added for incubation, namely 5 μL of a primary antibody is added into 10 mL of PBST according to a dilution ratio of 1:2000, and incubated on a shaking table at room temperature for 2h (or overnight at 4° C.); after incubation is completed, the sample is placed on a shaking table and washed with PBST for three times, wherein washing is conducted for 10 minutes each time;

8) a rabbit anti-mouse-HPR antibody is added for incubation, namely 5 μL of a secondary antibody is added into 10 mL of PBST, and incubated on a shaking table at room temperature for 1 hour; after incubation is completed, the sample is placed on a shaking table and washed with PBST for three times, wherein washing is conducted for 10 minutes each time; and 9) developing is conducted after the last time of washing is completed, and ECL developing solutions A and B in equal volume are mixed to form 1 mL in total; the staining solution is sucked by using a 1 mL pipette, and dropwise added onto the NC membrane, developing is conducted in a dark place for 5 minutes, developing is stopped by using pure water, and the NC membrane is aired, and stored in a dark place.

Embodiment 3

Figure 2:
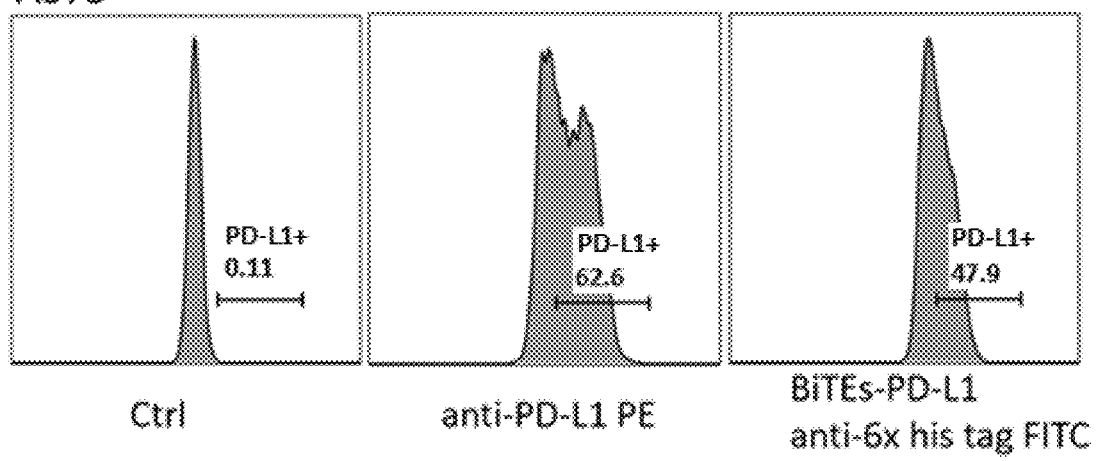
FIG. 2 is a flow cytometry diagram in a BiTEs-PD-L1 cell binding experiment.
Figure 2:
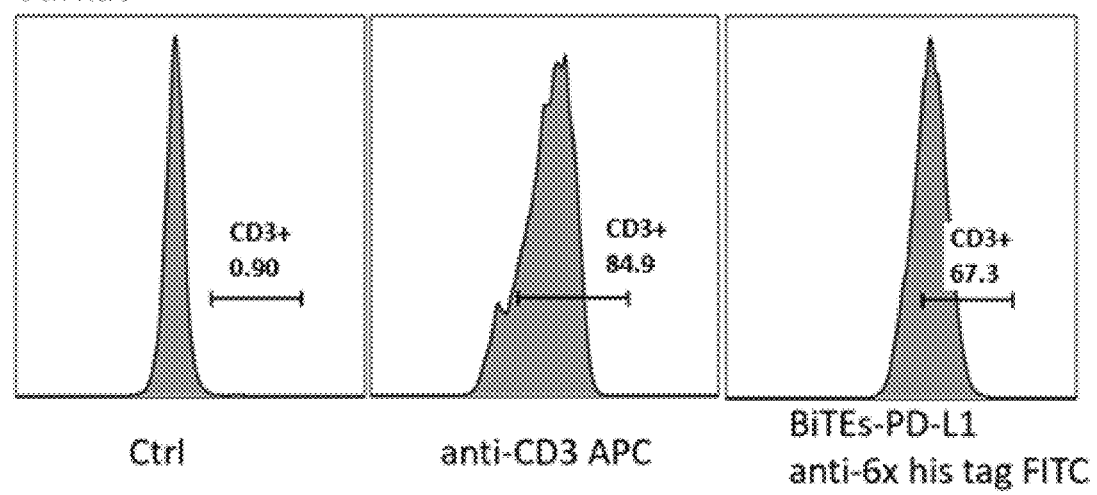

BiTEs-PD-L1 Cell Binding Assay $1 \times 10^6$ Jurkat cells and A375 cells are respectively resuspended in 100 μL of PBS buffer solution, the A375 cells are respectively incubated with 1 μg of human PD-L1 antibody and 500 μL of BiTEs-PD-L1 supernatant, the Jurkat cells are respectively incubated with 1 μg of human CD3 antibody and 500 μL of BiTEs-PD-L1 supernatant, incubation is carried out at 4° C. for 25 min, PBS is added for cleaning twice, 1 μg of 6×His-FITC antibody is added into a BiTEs-PD-L1 incubation group, incubation is carried out at 4° C. for 25 min, PBS is used for cleaning twice, up-flow detection is carried out, and the result is shown in FIG. 2.

Embodiment 4

Figure 3:
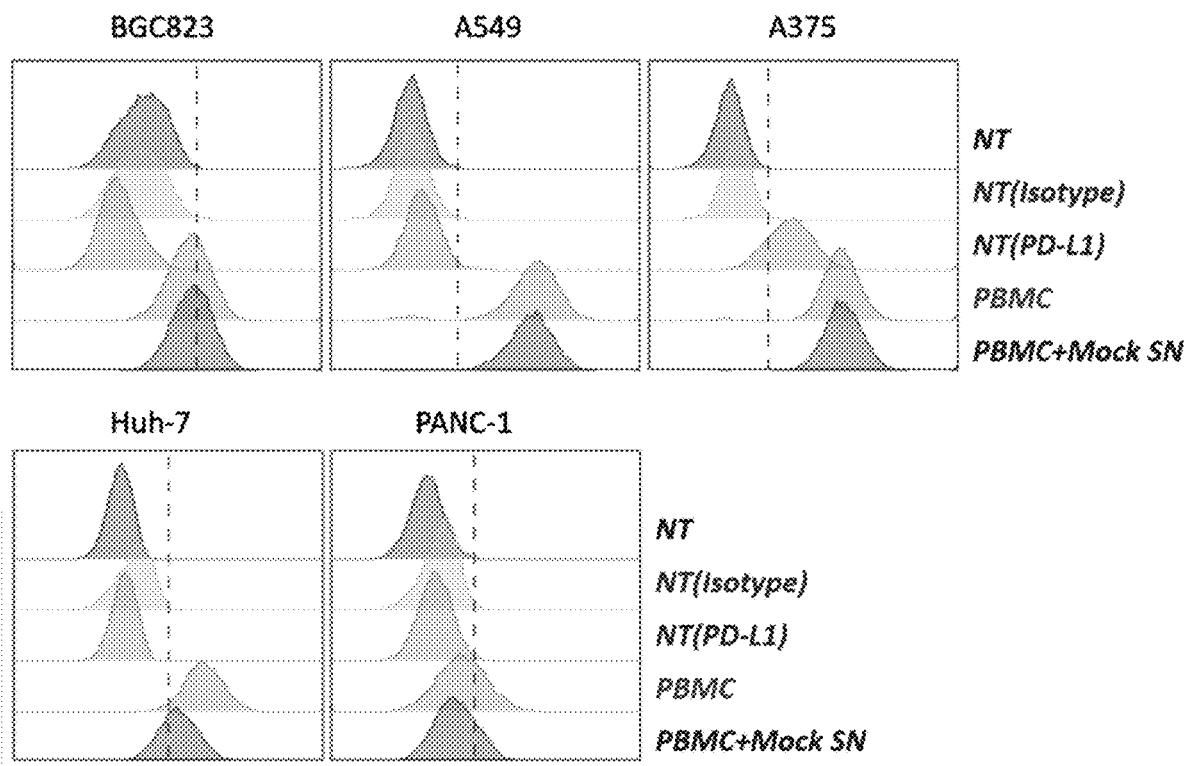
FIG. 3 is a flow cytometry diagram in a tumor cell PD-L1 expression detection experiment.
Figure 4:
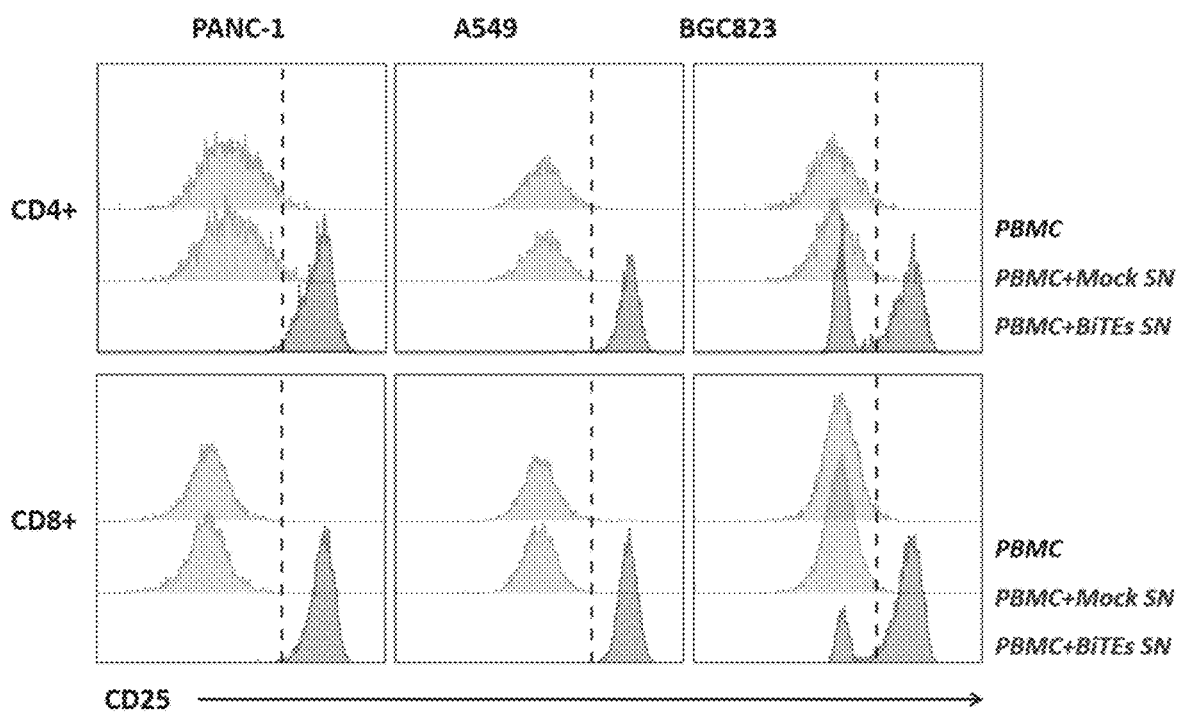
FIG. 4 is a flow cytometry diagram in a BiTEs-PD-L1 mediated PBMC (peripheral blood mononuclear cell) activation experiment.
Figure 5:
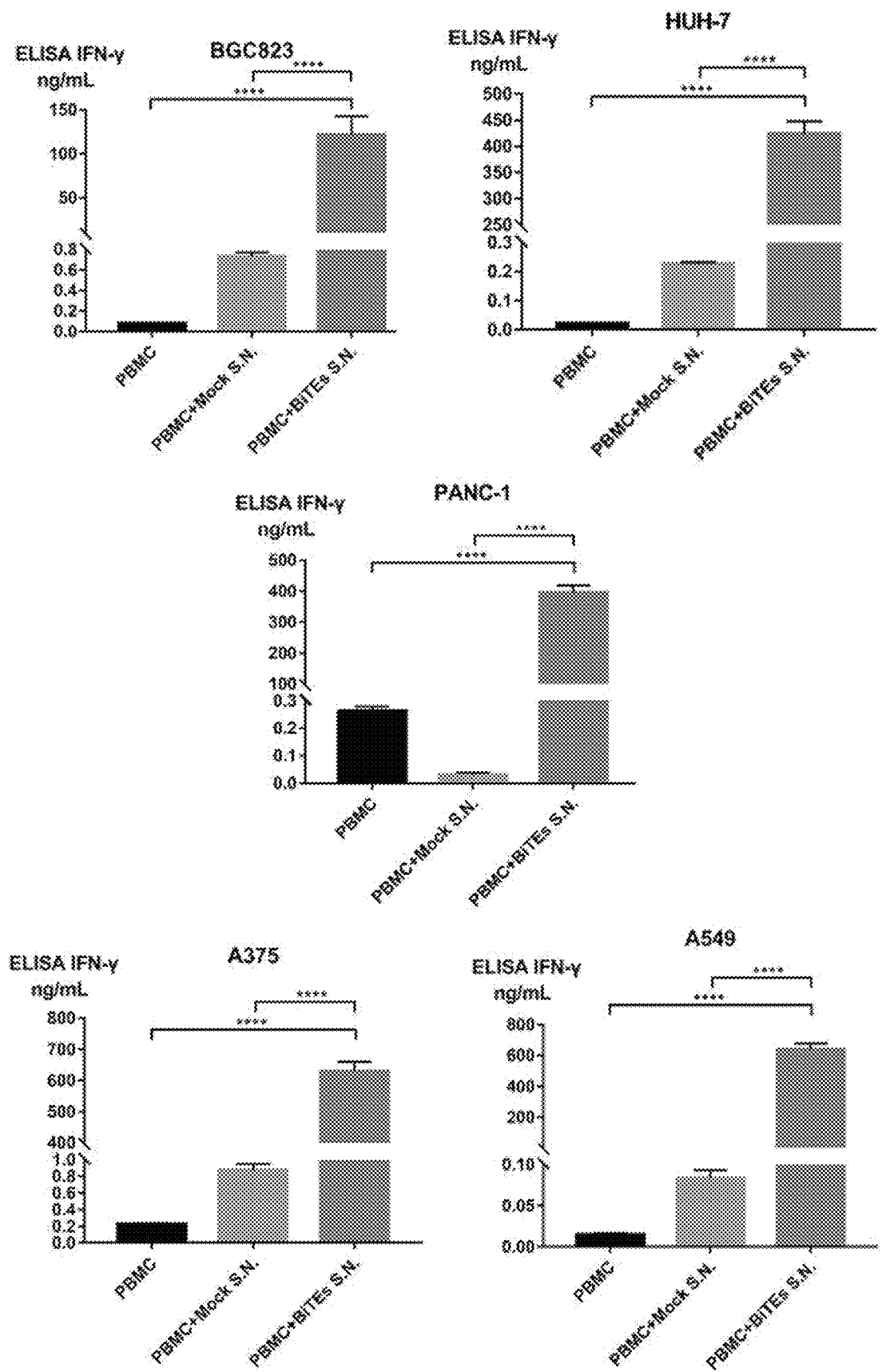
FIG. 5 is an IFN-γ detection result in a BiTEs-PD-L1 mediated PBMC activation experiment.
Figure 6:
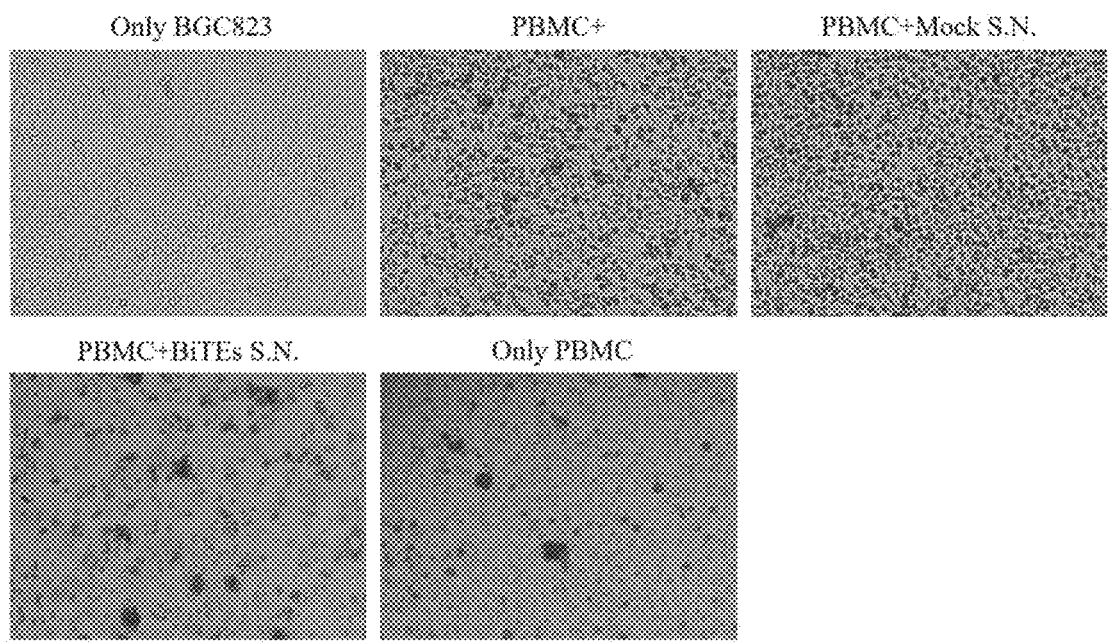
FIG. 6 is an effect comparison diagram of experimental results of killing the BGC823 cells by the BiTEs-PD-L1 mediated PBMC.
Figure 7:
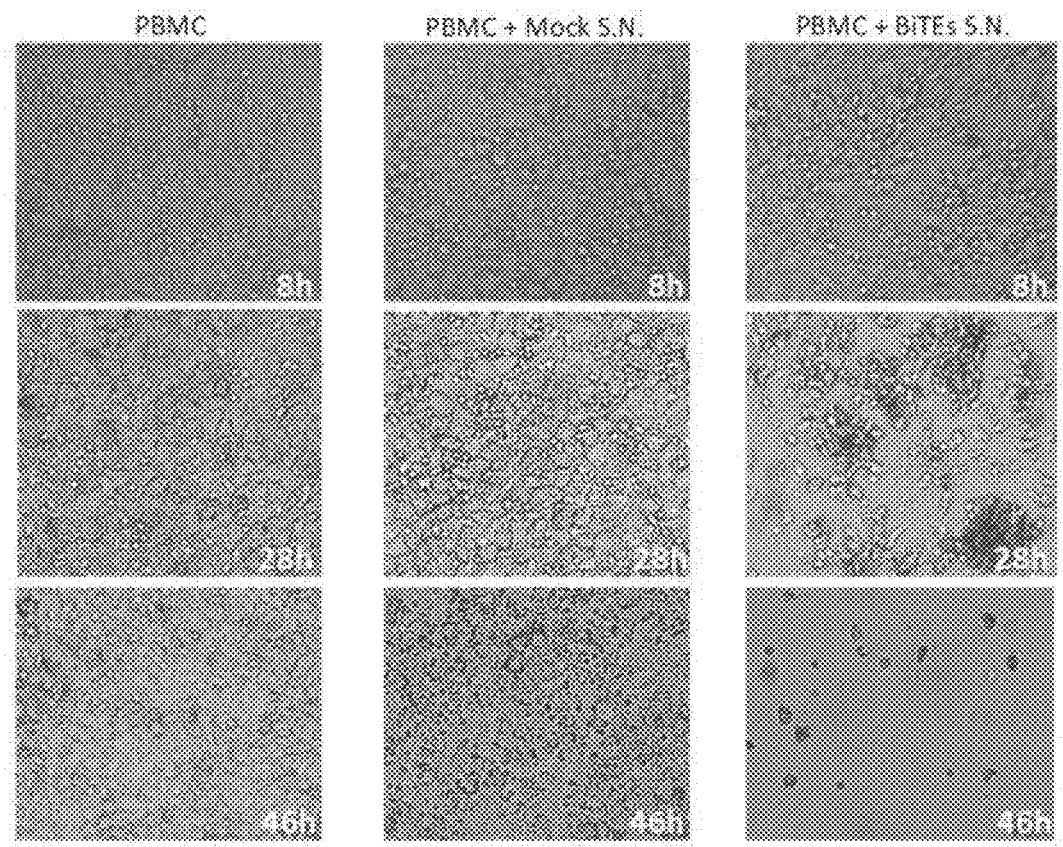
FIG. 7 is an effect comparison diagram of experimental results of killing the Huh-7 cells by the BiTEs-PD-L1 mediated PBMC.
Figure 8:
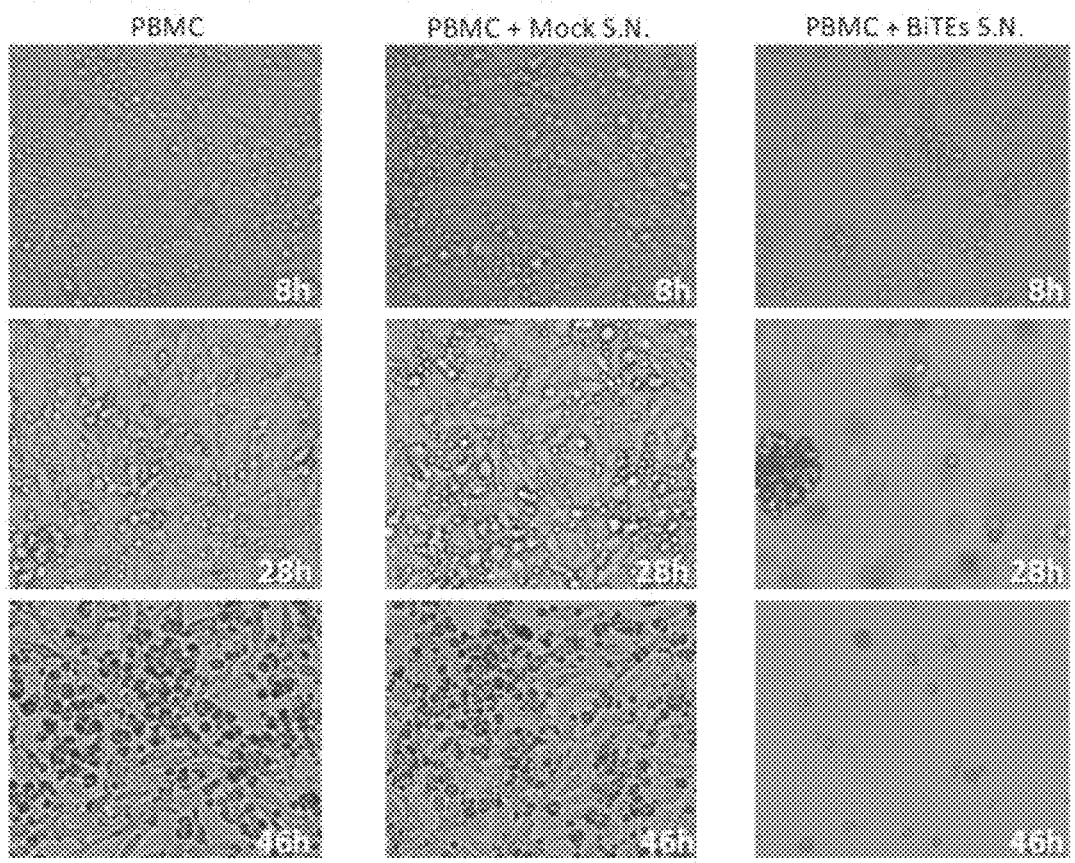
FIG. 8 is an effect comparison diagram of experimental results of killing A375 cells by the BiTEs-PD-L1 mediated PBMC.

1) Tumor Cell PD-L1 Expression Detection $2 \times 10^4$ Huh-7 cells, Panc-1 cells, BGC823 cells, A549 cells and A375 cells are laid in a 96-well plate and cultured overnight in a cell incubator with the temperature of 37° C. and the $CO_2$ concentration of 5%; PBMCs (peripheral blood mononuclear cells) are added according to an effect-target ratio of 2:1 on the next day, and culturing is conducted in a cell incubator with the temperature of 37° C. and the $CO_2$ concentration of 5% for 48 hours; the supernatant is removed, and PBS is added for cleaning twice; the tumor cells are digested by pancreatin, and the tumor cells are cleaned twice by PBS; the tumor cells are incubated with 1 μg of human PD-L1 antibody at 4° C. for 25 minutes, washing twice is conducted with PBS, up-flow detection is carried out, and the result is shown in FIG. 3;

2) BiTEs-PD-L1 Mediated PBMC Activation $2 \times 10^4$ Panc-1, BGC823 and A549 cells are laid in a 96-well plate and cultured overnight in a cell incubator with the temperature of 37° C. and the $CO_2$ concentration of 5%; Mock PBMC and BiTEs-PD-L1 incubated PBMC are respectively added according to an effect-target ratio of 2:1 on the next day, and culturing is conducted in a cell incubator with the temperature of 37° C. and the $CO_2$ concentration of 5% for 48 hours; the PBMCs in the supernatant are taken, washed twice by using PBS, incubated with 1 μg of human CD4, CD8 and CD25 antibodies at 4° C. for 25 minutes, and washed twice by using PBS, up-flow detection is carried out, and the result is shown in FIG. 4;

$2 \times 10^4$ Huh-7 cells, Panc-1 cells, BGC823 cells, A549 cells and A375 cells are laid in a 96-well plate and cultured overnight in a cell incubator with the temperature of 37° C. and the $CO_2$ concentration of 5%; Mock PBMC and BiTEs-PD-L1 incubated PBMC are respectively added according to an effect-target ratio of 2:1 on the next day, and culturing is conducted in a cell incubator with the temperature of 37° C. and the $CO_2$ concentration of 5% for 48 hours; a supernatant is taken, and centrifuged to remove cells; the IFN-γ in the supernatant is detected by using an Elisa kit, and the result is as shown in FIG. 5;

3) BiTEs-PD-L1 Mediated PBMC Killing $2 \times 10^4$ Huh-7 cells, BGC823 cells and A375 cells are laid in a 96-well plate and cultured overnight in a cell incubator with the temperature of 37° C. and the $CO_2$ concentration of 5%; Mock PBMC and BiTEs-PD-L1 incubated PBMC are respectively added according to an effect-target ratio of 2:1 on the next day, culturing is conducted in a cell incubator with the temperature of 37° C. and the $CO_2$ concentration of 5% for 48 hours, the killing condition is observed under a microscope, and the results are as shown in FIGS. 6-8.

Embodiment 5

A Process of oHSV2-BiTEs-PD-L1 Preparation 1) a 6-well plate is inoculated with $4 \times 10^5$ ICP4 cells, and the cells are cultured in a 5% $CO_2$ environment at 37° C.; a genome of oHSV2-GFP and a pHG52d34.5-CMV-BiTEs-PD-L1 plasmid are jointly transfected into the ICP4 cells by using a calcium phosphate transfection reagent on the next day, and whether toxic plaques are formed or not is observed after 24-48 hours; and 2) the cell wells with the toxic plaques are freeze-thawed for 5 minutes, centrifuging is conducted at 2000 g, a supernatant is collected, the supernatant is diluted by 100 times, 1000 times and 10000 times, and the ICP4 cells are infected; toxic plaques without green fluorescence are selected under a fluorescence microscope, the ICP4 cells are further infected, and toxic plaques without green fluorescence are repeatedly selected until the toxic plaques of the well plate do not have green fluorescence, so as to obtain the oHSV2-BiTEs-PD-L1; and a virus genome is further extracted, and the virus is identified by using PCR (Polymerase Chain Reaction).

Figure 9:
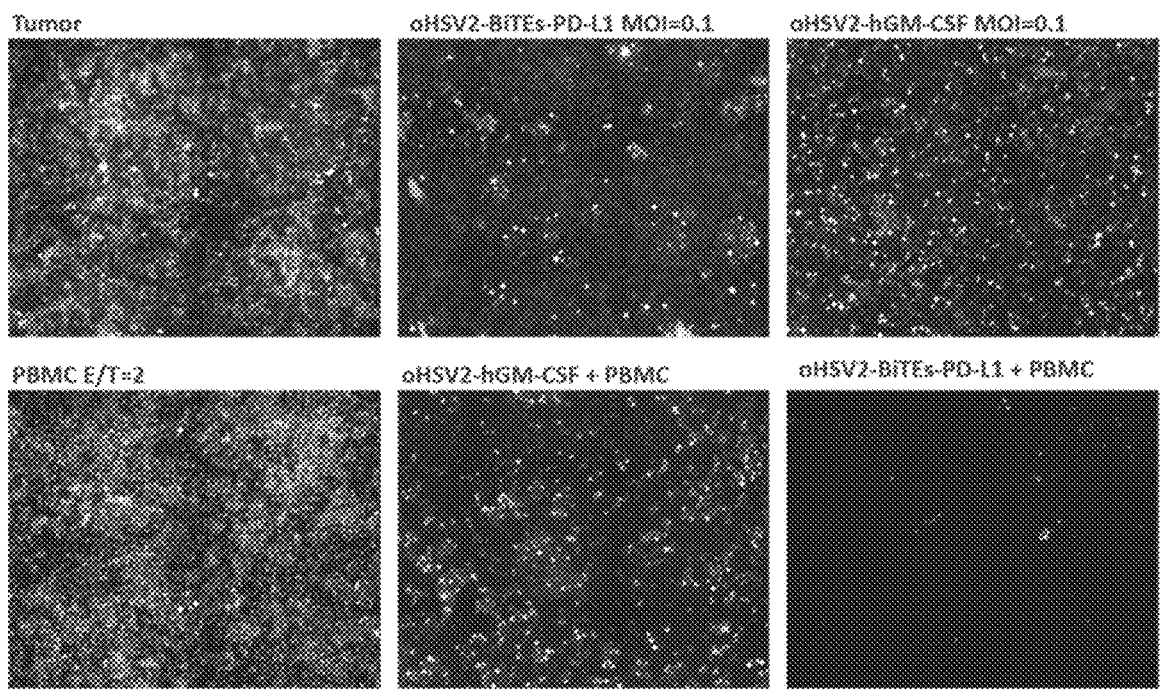
FIG. 9 is a high-throughput real-time imaging observation diagram in an oHSV2-BiTEs-PD-L1 combined PBMC killing experiment.
Figure 10:
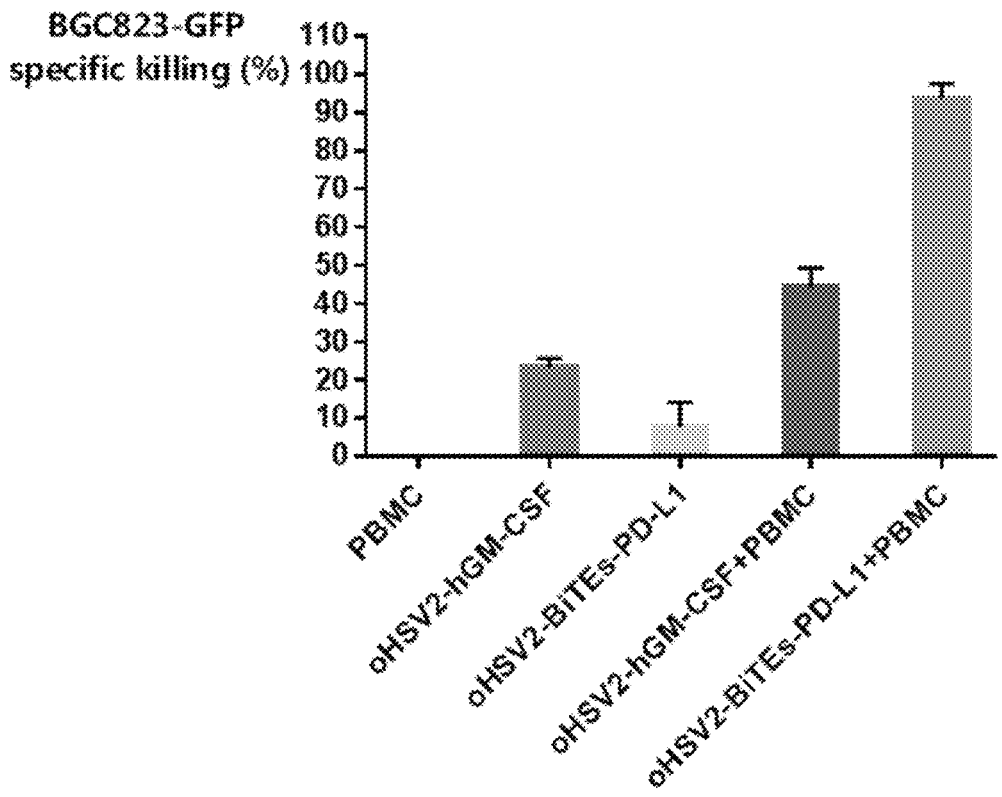
FIG. 10 is a data comparison graph of oHSV2-BiTEs-PD-L1 combined PBMC killing.

Embodiment 6 oHSV2-BiTEs-PD-L1 Combined PBMC Killing $2 \times 10^4$ BGC823-GFP cells are laid in a 96-well plate and cultured overnight in a cell incubator with the temperature of 37° C. and the $CO_2$ concentration of 5%; PBMCs (peripheral blood mononuclear cells) are respectively added according to an effect-target ratio of 2:1 on the next day, meanwhile, oHSV2-hGM-CSF and oHSV2-BiTEs-PD-L1 are added according to MOI=0.1, groups are shown in Table 1 below, the cells are observed by using a high-throughput real-time imaging system, and the results are as shown in FIG. 9 and FIG. 10.

TABLE 1

| oHSV2-BiTEs-PD-L1 combined PBMC killing experiment grouping ||
| --- | --- |
| Group | Killing Rate |
| PBMC | 0% |
| oHSV2-hGM-CSF | 23.33% |
| oHSV2-BiTEs-PD-L1 | 7.756% |
| oHSV2-hGM-CSF + PBMC | 44.20% |
| oHSV2-BiTEs-PD-L1 + PBMC | 93.77% |

The oHSV2-hGM-CSF involved in the embodiments was preserved in the China General Microbiological Culture Collection Center (CGMCC, No. 3, yard 1, Beichen West Road, Chaoyang District, Beijing, China) on Feb. 3, 2010. The accession number is CGMCC no. 3600. The preserved biomaterial is H2d3d4-hGF strain, and its strain number means: H2 refers to herpes simplex virus type II HG52 strain (oHSV2); d3 refers to the elimination of ICP34.5; d4 refers to the elimination of ICP47; hGF refers to the insertion of human granulocyte macrophage colony stimulating factor (hGM-CSF) expression box. (The above information is disclosed in Chinese invention patent CN201010116275.3 "Recombinant Type II Herpes Simplex Virus Vector, Preparation Method for Same, Recombinant Virus, Pharmaceutical Composition and Application)

Part II Virus Composition

The oHSV2-hGM-CSF involved in the following embodiments is the same as that in embodiment 6, it can also be abbreviated as oHSV2-GMCSF, and then based on the oHSV2-hGM-CSF, a series of oncolytic viruses were constructed by inserting foreign therapeutic genes into ICP 34.5 sites, see the table below.

TABLE 2

| Serial Number | Full Name of Virus | Foreign Gene | Foreign Gene Sequence Source/Sequence Number |
|---|---|---|---|
| 1 | oHSV2-BiTEs-PD-L1 | BiTEs-PD-L1 | SEQ ID No. 1 |
| 2 | oHSV2-OX40L | OX40L | GenBank: BC153120.1 |
| 3 | oHSV2-IL12 | IL12 | SEQ ID No. 2 |
| 4 | oHSV2-neo | neo | SEQ ID No. 3 |
| 5 | oHSV2-IL15 | IL15 | NCBI Reference Sequence: NM_001254747.1 |
| 6 | oHSV2-PD1v | PD1v | SEQ ID No. 4 |
| 7 | oHSV2-antiPD1 | antiPD1 | SEQ ID No. 5 |

Embodiment 7

1. Experimental Purpose

The anti-tumor effects of various oncolytic viruses were compared in BALB/c tumor bearing mouse model of mouse colon cancer cell CT26-iRFP.

In order to simplify the identification in the figures, The virus name of the experimental group is abbreviated as follows: oHSV2-hGM-CSF (hGM-CSF), oHSV2-IL15 (IL15), oHSV2-IL12 (IL12), oHSV2-PD1v (PD1v), oHSV2-antiPD1 (antiPD1) and oHSV2-neo (neo).

The tumor formation was induced by subcutaneous injection of mouse colon cancer cells (CT26) into the right costal abdomen of BALB/c mice, and randomly grouping, including negative control group (Control). The treatment was started when the tumor volume reached about 120 mm³. The first treatment was on the first day. The corresponding viruses were injected into the tumor of the experimental groups, and the Inositol Sorbitol Buffer (IS buffer is generally used to resuspend virus) was injected into the tumor of the Control group (IS buffer is a common reagent, which can be sold on the market or prepared by ourselves, and its composition difference will not affect the experimental results). The treatment was carried out for 3 times (on the 1st/4th/7th day). After the first injection, the test mice were observed.

2. Experimental Principle

The experimental principle refers to Standard Operating Procedures [CT26 tumor cell culture SOP] and [inducing CT26 tumor in vivo SOP].

3. Experimental Design and Methods 3.1 Experimental Materials, Animal Reagents and Consumables Viruses: all viruses are produced according to the same standard scheme. All viruses were resuspended in the preparation buffer and sub frozen in the refrigerator at −70° C. for rapid thawing before use.

Animals: female BALB/c normal mice were purchased from Hubei Food And Drug Safety Evaluation Center and raised in a pathogen free animal laboratory. The size of animals at the time of administration was 5-7 weeks (weight 16-20 g). It was distinguished by marking the mouse tail.

3.2 Experimental Methods 3.2.1 Preparation of CT26 Cells

Colon cancer cells derived from mice were cultured according to the standard protocol (CT26-iRFP, purchased from the National Experimental Cell Resource Sharing Platform. CT26-iRFP was modified on the basis of parental cells to continuously express near-infrared fluorescent protein). The culture medium was DMEM/F12 containing 10% fetal bovine serum. Before tumor induction, the cells were collected, centrifuged at 820 g for 5 min, and then remixed with serum-free DMEM/F12.

3.2.2 Tumor Model

Tumor induction, female BALB/c normal mice (7-9 mice in each group) were injected subcutaneously into the right costal abdomen with 100 µl cell suspension containing $2 \times 10^6$ CT26 mouse colon cancer cell. Then measure the long diameter (a) and short diameter (b) of the tumor every day. The calculation formula of tumor volume (TV) is: $V = \frac{1}{2} \times a \times b^2$. The a and b represent length and width, respectively.

3.2.3 Virus Therapy

When the average tumor volume reached about 120 mm³, the treatment was started. The first treatment was on the first day. On the first, fourth and seventh days, the tumor bearing mice in the treatment group were injected with the corresponding virus ($2 \times 10^5$ $CCID_{50}$/100 µl/piece); The two Control groups of tumor bearing mice were injected with equal volume of IS buffer (100 µl).

E6 (evaluation of the effect of single virus in the treatment of CT26-iRFP): dilute the virus with IS buffer to a titer of $1 \times 10^7$ $CCID_{50}$/ml, and administrate 100 µl to each mouse, that is, administrate $1 \times 10^6$ $CCID_{50}$ to each mouse.

E5 (cocktail virus comparison): dilute the virus with IS buffer to a titer of $1 \times 10^6$ $CCID_{50}$/ml, and administrate 100 µl to each mouse, that is, administrate $1 \times 10^5$ $CCID_{50}$ to each mouse.

Cocktail virus: first dilute several viruses to the target titer, and then mix several required viruses one by one. The mixed virus is called cocktail virus.

Figure 13:
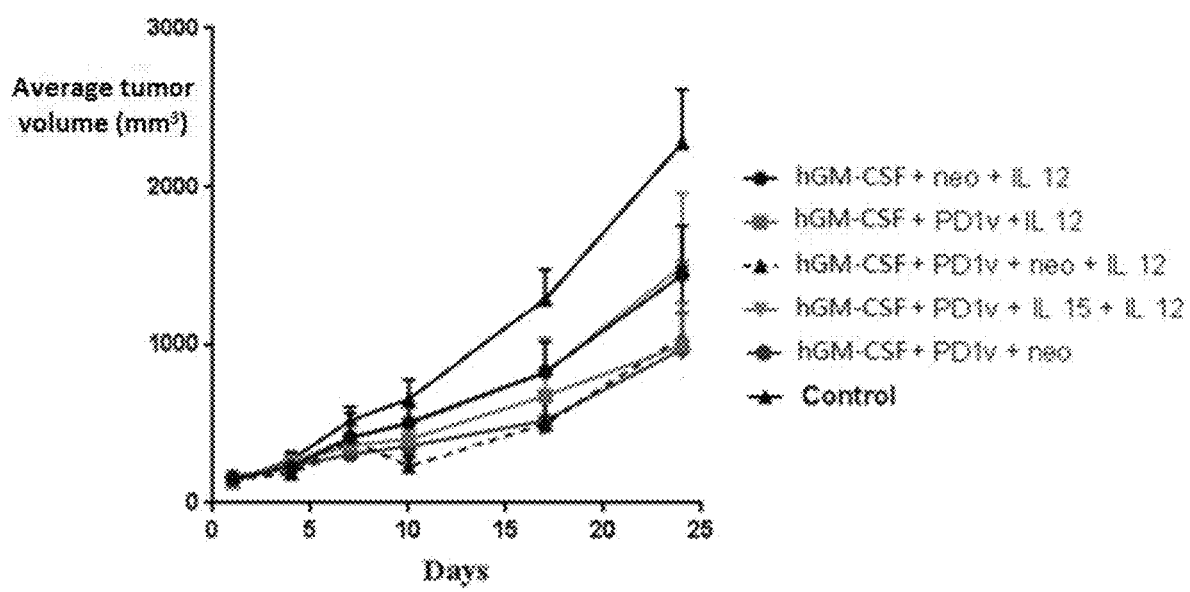
FIG. 13 is an overall effect comparison diagram of various viruses in the treatment of mouse colon cancer CT26-iRFP.
Figure 14:
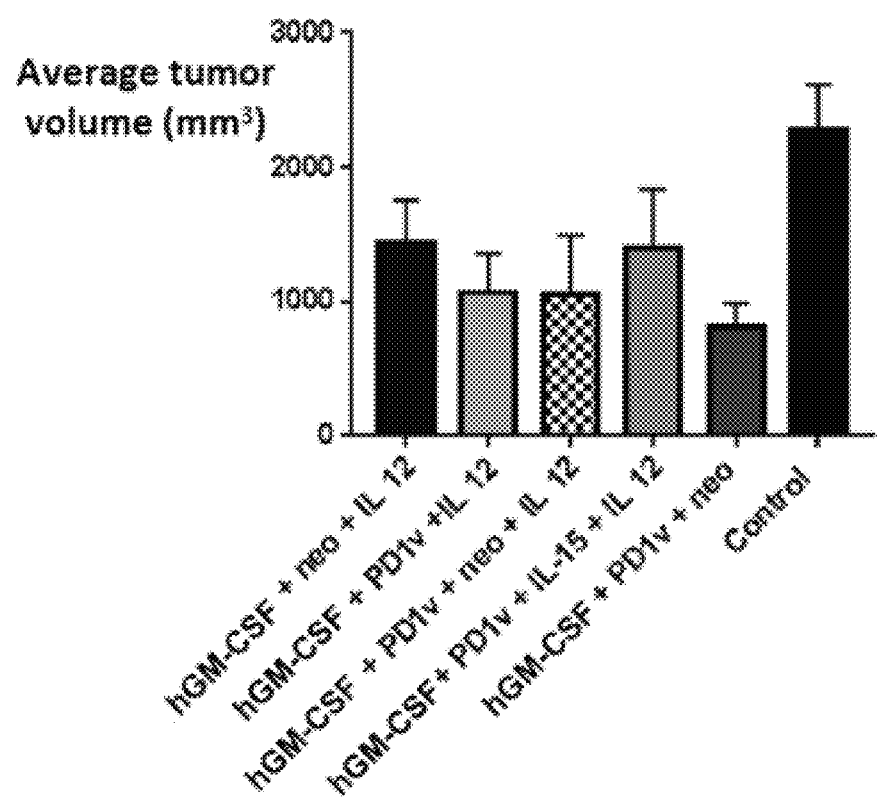
FIG. 14 is an effect comparison diagram of various viruses on the 24th day in the treatment of mouse colon cancer CT26-iRFP.

The grouping identification in the figure has been simplified, as shown in FIG. 13 and FIG. 14, the hGM-CSF+PD1v+neo group means that after diluting the three viruses oHSV2-hGM-CSF, oHSV2-PD1v and oHSV2-neo to $1 \times 10^6$ $CCID_{50}$/ml, 1 ml of each virus is mixed together to obtain the final 3 ml cocktail virus.

4. Evaluation Criteria for the Effectiveness of Experimental Results

The data were processed by statistical software and expressed by Mean±SEM. One way ANOVA was used for comparison between groups. $P<0.05$ means statistical significance.

Figure 11:
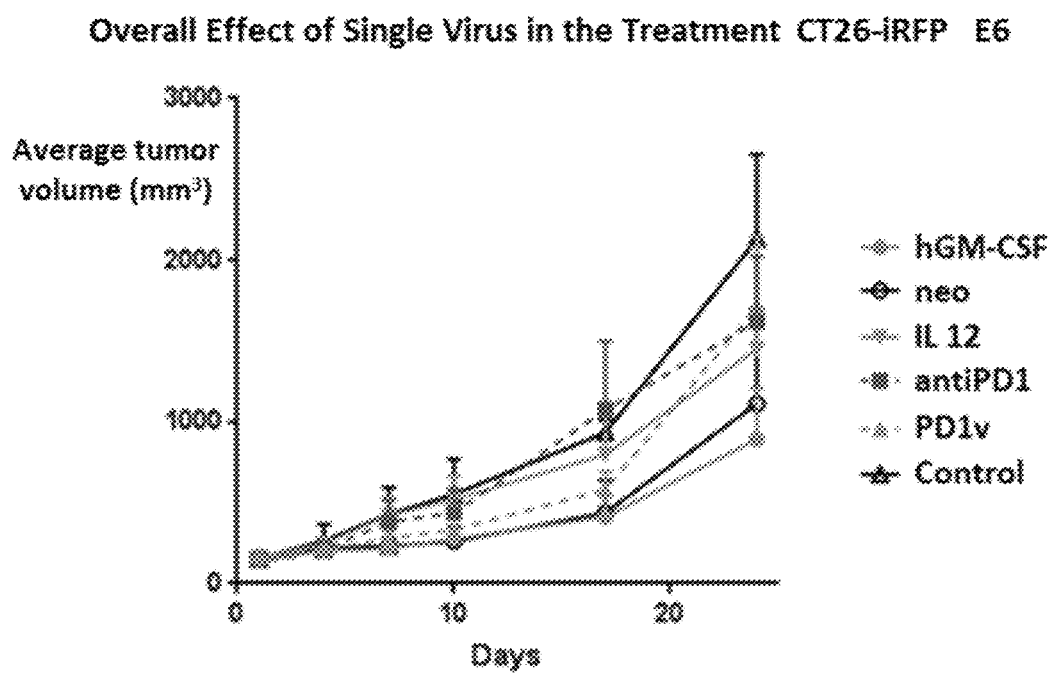
FIG. 11 is an overall effect comparison diagram of single virus in the treatment of mouse colon cancer CT26-iRFP.
Figure 12:
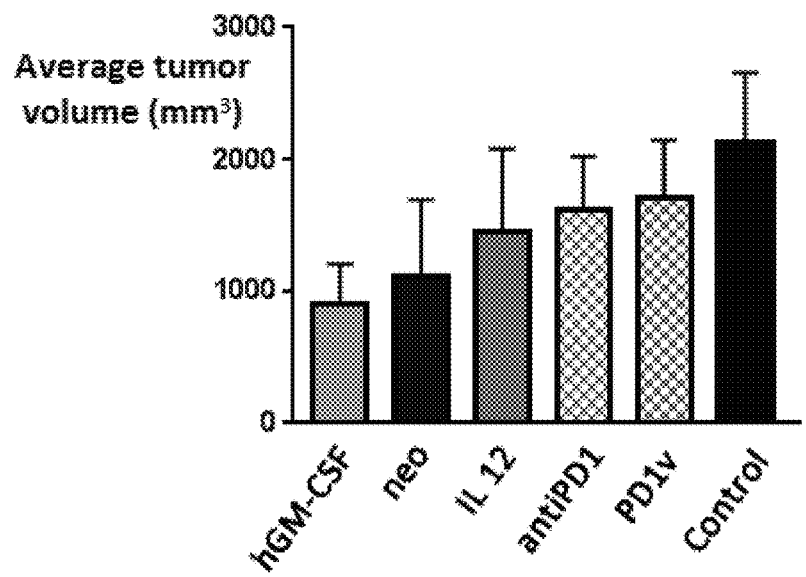
FIG. 12 is an effect comparison diagram of single virus on the 24th day in the treatment of mouse colon cancer CT26-iRFP.

The grouping experiment results are shown in FIGS. 11 to 15 (the results of single virus treatment are shown in FIG. 11 and FIG. 12, and the results of cocktail virus treatment are shown in FIG. 13 and FIG. 14). IL12 and IL15 activate T and NK cells respectively. PD1v can bind to PD-L1 with high affinity and block the negative regulation of PD-1/PD-L1. Then, the antitumor efficacy of a series of oncolytic viruses in vivo and in vitro was evaluated. Using the colon cancer bearing mouse model (CT26-iRFP) expressing near infrared red fluorescent protein, the therapeutic effects of oHSV2 carrying foreign gene were compared by intratumoral injection. The results showed that oHSV2-hGM-CSF and oHSV2-neo had the most obvious antitumor effect compared with other viruses.

Figure 15:
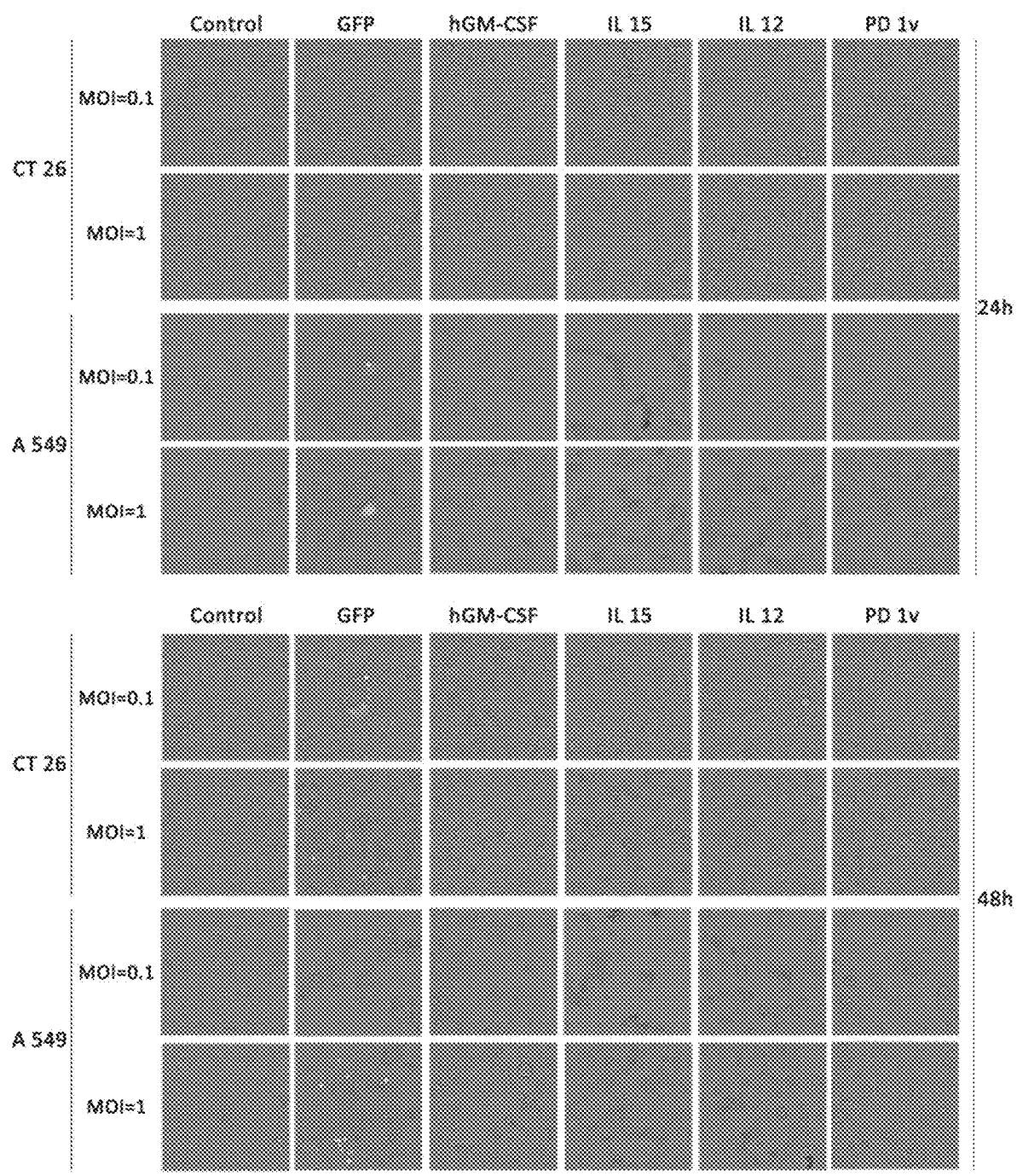
FIG. 15 shows the comparison of cell killing results.

It can be observed from FIG. 15 that in vitro killing experiments were carried out on A549 cells and CT26 cells infected with oncolytic viruses carrying different exogenous factors with MOI of 0.1 and 1. At 24 h and 48h, compared with the Control group, the tumor cells in the experimental group showed different degrees of morphological changes and even death. It is suggested that oncolytic virus has tumor cell killing effect in vitro.

Embodiment 8

Cocktail Virus Treatment Experiment
1. Experimental Purpose
BALB/c tumor bearing mouse model of mouse colon cancer cell CT26-hPDL1 was used to compare various virus compositions.
2. Experimental Materials
Tumor cell line: CT26-hPDL1 (GFP expression 99.8% and hPDL1 expression 73.4%, purchased from the National Experimental Cell Resource Sharing Platform. CT26-hPDL1 is modified on the basis of parent cells to continuously express human PDL1 protein)
Mice: 130 female BALB/c mice (6-8 weeks old)
oHSV2 virus: dilute the virus with IS buffer to a titer of $1\times10^7$ $CCID_{50}$/ml, and administrate 100 μl to each mouse, that is, administrate $1\times10^6$ $CCID_{50}$ to each mouse.
3. Experimental Steps
Administration Time: intratumoral injection, administration on days 1, 4 and 7, and other unspecified steps are the same as those in embodiment 7.

TABLE 3

| Grouping | |
|---|---|
| Group number | Administered Virus/Virus Mixture |
| 1 | oHSV2-BiTEs-PD-L1 |
| 2 | oHSV2-hGM-CSF |
| 3 | oHSV2-OX40L |

TABLE 3-continued

| Grouping | |
|---|---|
| Group number | Administered Virus/Virus Mixture |
| 4 | oHSV2-PD1v |
| 5 | oHSV2-neo |
| 6 | oHSV2-IL12 |
| 7 | oHSV2-hGM-CSF + oHSV2-BiTEs-PD-L1 |
| 8 | oHSV2-OX40L + oHSV2-BiTEs-PD-L1 |
| 9 | oHSV2-hGM-CSF + oHSV2-OX40L |
| 10 | oHSV2-OX40L + oHSV2-BiTEs-PD-L1 + oHSV2-hGM-CSF |
| 11 | oHSV2-PD1v + oHSV2-neo + oHSV2-hGM-CSF |
| 12 | oHSV2-BiTEs-PD-L1 + oHSV2-hGM-CSF + oHSV2-OX40L + oHSV2-PD1v + oHSV2-neo + oHSV2-IL12 |
| 13 | IS Buffer |

In the group name shown in the figures, except oHSV2-BiTEs-PD-L1 is abbreviated as BiTEs, oHSV2-OX40L is abbreviated as OX40L, Group 12 is abbreviated as 6mix, and other viruses are abbreviated as in embodiment 7.

4. Experimental Data Collection: The First Treatment Time was Recorded as the First Day, and then the Long Diameter and Short Diameter of the Tumor were Measured on the 1st, 4th, 7th, 10th, 14th, 21st and 28th Days of Treatment.

Figure 16:
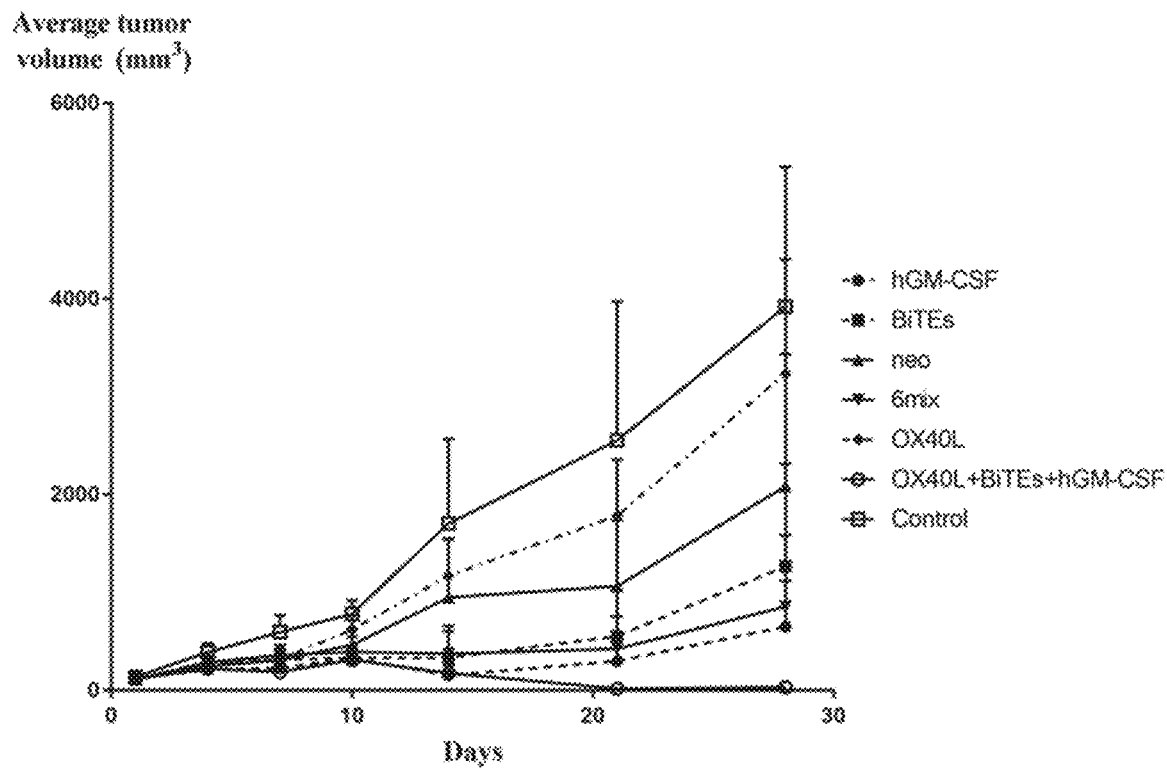
FIG. 16 is an overall effect comparison diagram of various viruses in the treatment of mouse colon cancer CT26-hPDL1.
Figure 17:
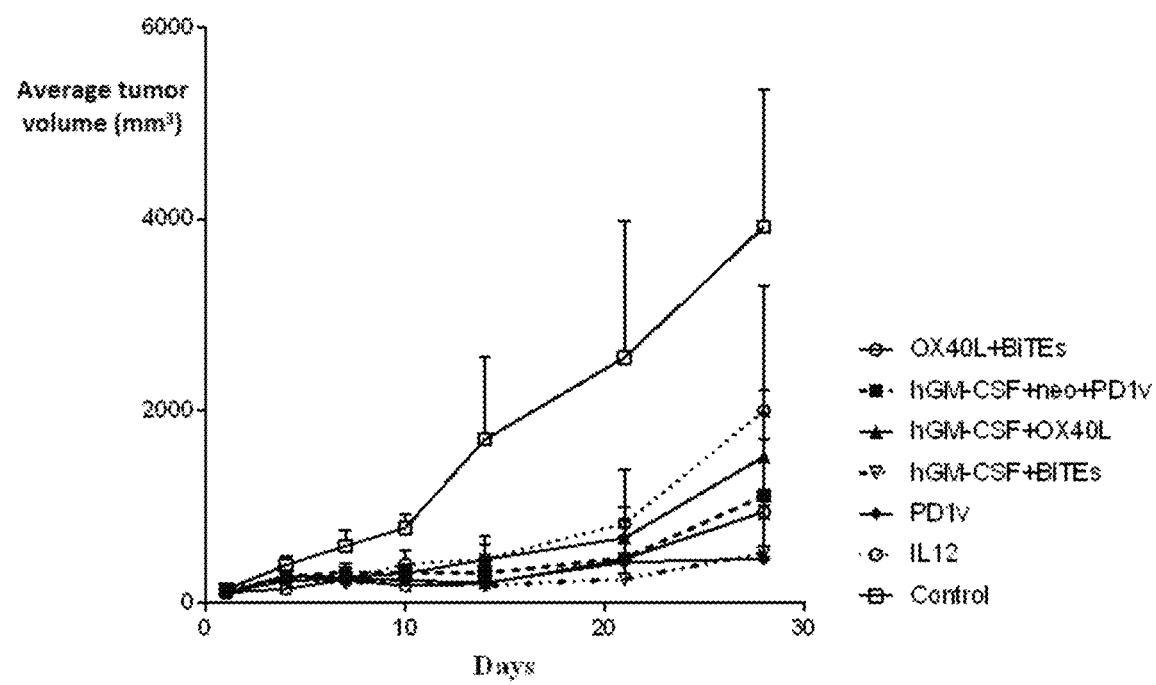
FIG. 17 is an overall effect comparison diagram of various viruses in the treatment of mouse colon cancer CT26-hPDL1.
Figure 18:
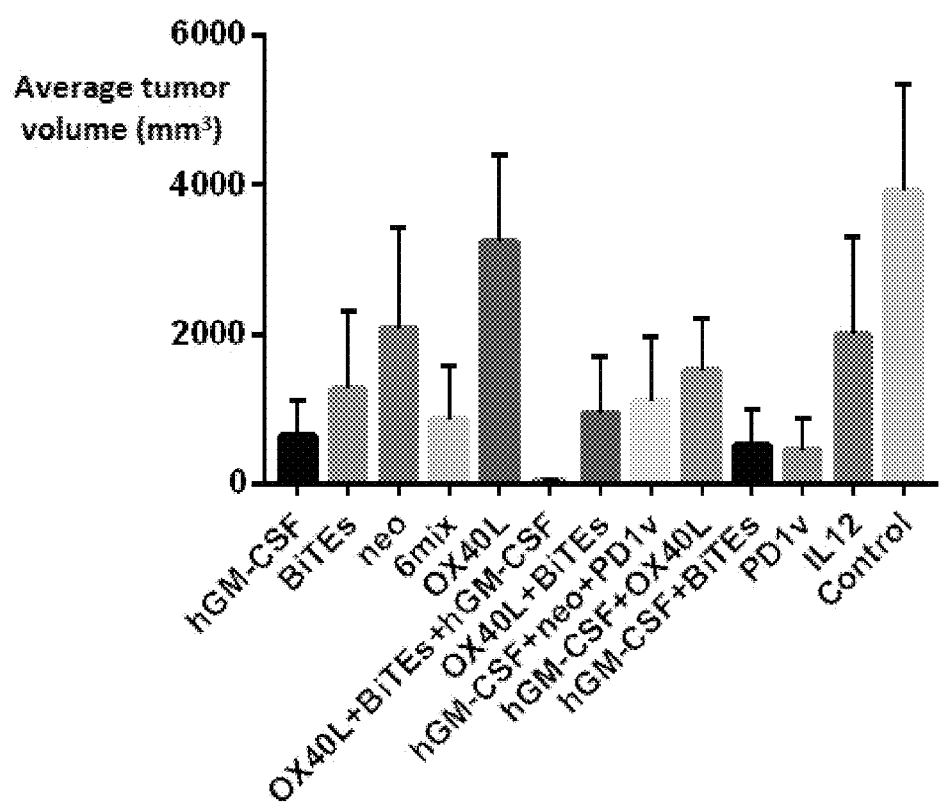
FIG. 18 is a comparison diagram of the average tumor size on the 28th day in the treatment of mouse colon cancer CT26-hPDL1 with various viruses.

The results are shown in the following table and FIGS. 16~18.

TABLE 4

| Tumor Growth Data of Virus Treatment Group | | |
|---|---|---|
| Group | Survival Rate | Tumor Clearance |
| hGM-CSF | 80.00% | 60.00% |
| BiTEs | 80.00% | 80.00% |
| neo | 77.80% | 44.40% |
| 6 mix | 88.90% | 77.80% |
| OX40L | 40.00% | 30.00% |
| OX40L + BiTEs + hGM-CSF | 100.00% | 80.00% |
| OX40L + BiTEs | 80.00% | 80.00% |
| hGM-CSF + neo + PD1v | 80.00% | 70.00% |
| hGM-CSF + OX40L | 60.00% | 50.00% |
| hGM-CSF + BiTEs | 90.00% | 60.00% |
| PD1v | 80.00% | 70.00% |
| IL12 | 60.00% | 40.00% |
| Control | 44.40% | 0.00% |

The results showed that in general, the effect of virus composition therapy was better than that of single virus group, especially the survival rate of OX40L+BiTEs+hGM-CSF group was higher, which was more effective in inhibiting tumor growth. Its comprehensive effect was even stronger than that of 6mix group, and other groups such as hGM-CSF+BiTEs also had better effects. These data show that the combination therapy of multiple viruses loaded with foreign genes has strong antitumor effect, but the number of foreign genes was not the more the better.

What is claimed is:

1. A bispecific single-chain antibody, comprising the amino acid sequence of SEQ ID NO: 1.

2. A recombinant oncolytic virus, comprising a herpes simplex virus type II as a vector, and a gene encoding a bispecific single-chain antibody comprising the amino acid sequence of SEQ ID NO: 1 integrated in the vector.

3. A composition, comprising two or more recombinant herpes simplex viruses loaded with different functional genes, one of which is the recombinant oncolytic virus according to claim 2.

* * * * *